(12) United States Patent
Eaton

(10) Patent No.: US 7,721,350 B1
(45) Date of Patent: May 25, 2010

(54) MOLDED PHOTOTHERAPY GOGGLES

(75) Inventor: Jason P. Eaton, Hunker, PA (US)

(73) Assignee: Ric Investments, LLC, Wilmington, DE (US)

( * ) Notice: Subject to any disclaimer, the term of this patent is extended or adjusted under 35 U.S.C. 154(b) by 0 days.

(21) Appl. No.: 11/731,545

(22) Filed: Mar. 30, 2007

Related U.S. Application Data

(60) Provisional application No. 60/787,739, filed on Mar. 31, 2006.

(51) Int. Cl.
*A61F 9/00* (2006.01)
(52) U.S. Cl. .......................................... 2/15
(58) Field of Classification Search ................ 2/12, 2/15; 128/858; 607/109
See application file for complete search history.

(56) References Cited

U.S. PATENT DOCUMENTS

| | | | | |
|---|---|---|---|---|
| 2,243,982 | A * | 6/1941 | Seeley | 2/12 |
| 4,122,847 | A * | 10/1978 | Craig | 128/858 |
| 4,411,263 | A | 10/1983 | Cook | |
| 4,502,476 | A * | 3/1985 | Welt | 128/858 |
| 4,644,588 | A | 2/1987 | Zawacki | |
| 4,649,908 | A * | 3/1987 | Ghaly | 128/858 |
| 4,872,217 | A * | 10/1989 | Kitayama | 2/15 |
| 4,908,878 | A * | 3/1990 | Tarragano | 2/15 |
| 5,046,200 | A * | 9/1991 | Feder | 2/452 |
| 5,307,523 | A * | 5/1994 | Lewis et al. | 2/433 |
| 5,425,380 | A * | 6/1995 | Hudson et al. | 128/858 |
| 5,613,502 | A | 3/1997 | Lee | |
| 6,571,799 | B1 * | 6/2003 | Daly | 128/857 |
| 6,745,397 | B2 * | 6/2004 | Magidson | 2/15 |
| 6,880,177 | B2 * | 4/2005 | Sung | 2/440 |

OTHER PUBLICATIONS

Small Beginnings, "Bili-Bonnet phototherapy Mask", www.small-beginnings.com, 1 pg., Date Unavailable.

* cited by examiner

*Primary Examiner*—Katherine Moran
(74) *Attorney, Agent, or Firm*—Timothy A. Nathan

(57) ABSTRACT

Phototherapy goggles for infants undergoing phototherapy. The goggles include a eye covering to cover the eyes of the infant and a headgear assembly to prevent the eye covering from becoming misaligned. The eye covering is formed to correspond to the anatomical contours of the infant's face and the headgear includes an elastomeric layer with a high coefficient of friction to further prevent the phototherapy goggles from becoming misaligned.

20 Claims, 10 Drawing Sheets

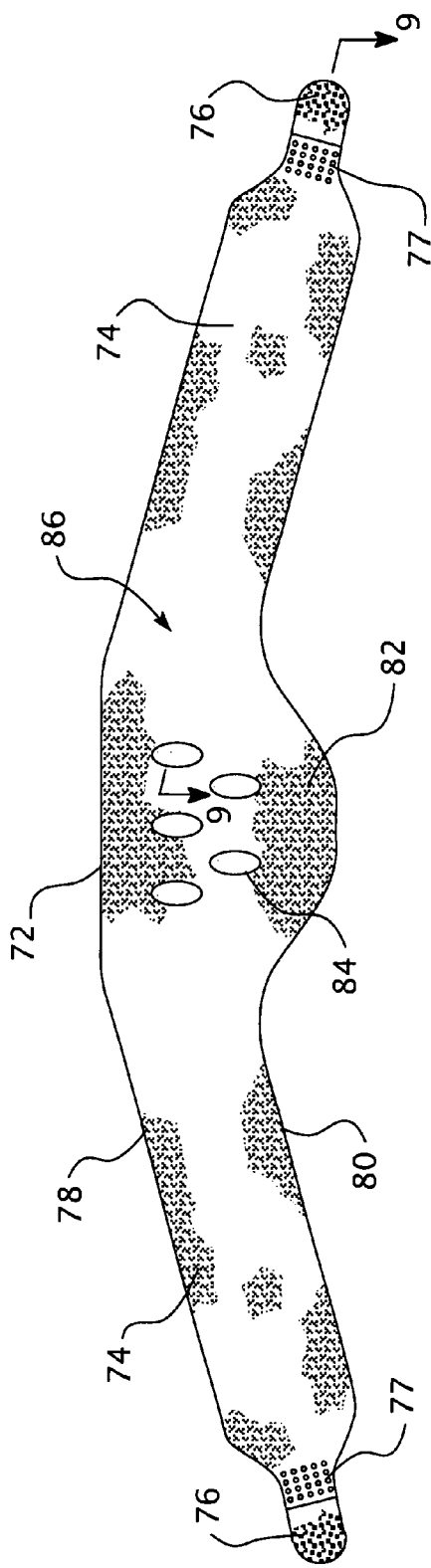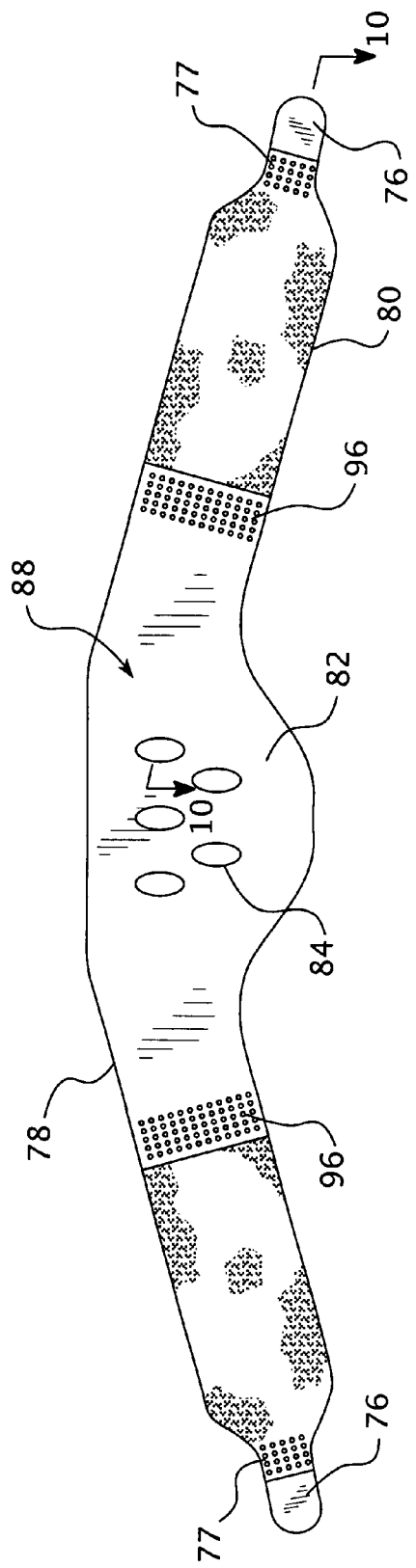

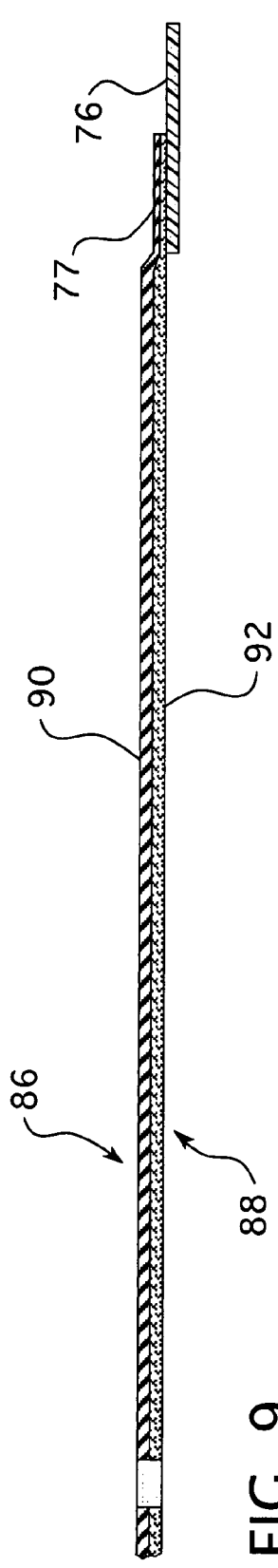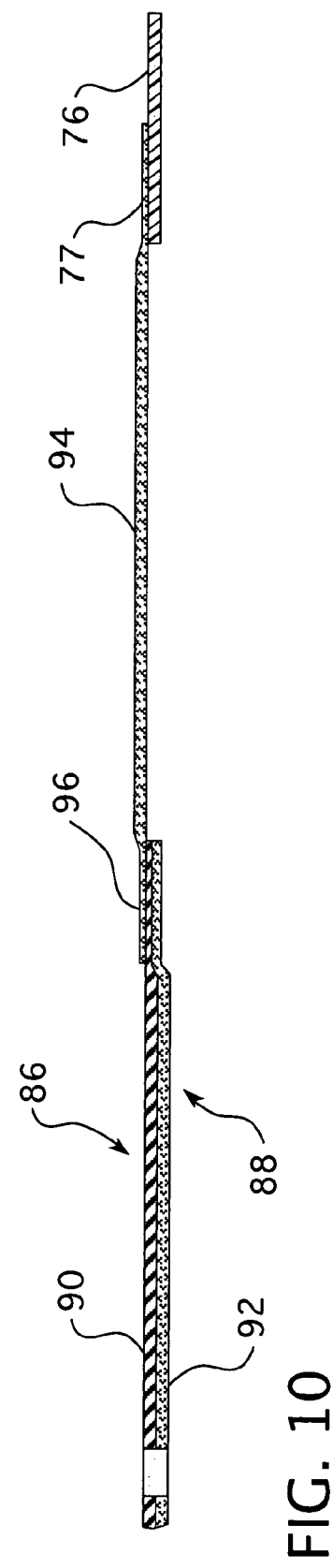

MOLDED PHOTOTHERAPY GOGGLES

CROSS-REFERENCE TO RELATED APPLICATIONS

This application claims priority under 35 U.S.C. §119(e) from provisional U.S. patent application No. 60/787,739 filed Mar. 31, 2006 the contents of which are incorporated herein by reference.

BACKGROUND OF THE INVENTION

1. Field of the Invention

This invention relates to phototherapy goggles and, more particularly, to phototherapy goggles that protect the eyes of an infant.

2. Description of the Related Art

Certain medical treatments can be harmful to the eyes. For example, children born with jaundice have yellow-colored skin due to the presence of high amounts of bilirubin in the blood. Traditional treatment consists of phototherapy in the form of prolonged exposure to high doses of light, and specifically blue light of 425-470 nm wavelength. While light exposure accelerates the removal of excess bilirubin from the infant's body, it can be harmful to the infant's eyes, especially in the high dosages currently employed.

Ultraviolet light, which is usually incidentally emitted, is known to induce keratitis, conjunctivitis, or lens opacities. Wavelengths of visible light, for example, the broad wavelength range of 400-780 nm including the aforementioned blue light range, and near infrared (780-1400 nm), are known to cause photothermal damage at high levels of irradiance. It has also been suggested that exposure of preterm infants' eyes to even ambient light of high intensity may increase the incidence of retinopathy of prematurity by increasing the toxic effects of oxygen.

Therefore, phototherapy goggles, or masks, shaped to generally cover the eyes are used during treatment in an attempt to eliminate or reduce the amount of light the infant's eyes are exposed to. Many conventional masks are designed to seal light out by cinching a flat, fabric-like covering against the eyes. Examples of this approach to infant mask design are disclosed in U.S. Pat. Nos. 4,411,263; 4,502,476; and 4,644,588. As may be appreciated by those of ordinary skill in the art, snug conformance of the mask material to the infant's head will place direct pressure on the eyeball and eyelid, while a loose-fitting mask leaks light about its periphery and may pose the hazard of occluding the infant's nostrils if slippage of the mask occurs. Thus, existing masks may be uncomfortable because they do not allow the eyelid to move normally and, more significantly, they may cause increased ocular pressure. Further, existing flat mask designs often leak from the side and therefore do not adequately protect the infant's eyes from light.

Other masks are known in the art such as the one described in U.S. Pat. No. 5,613,502 ("the '502 patent"). The mask described in this patent once again utilizes a large one-piece protective eye covering formed from three layers of material. The outer layers of the eye covering are formed from a soft napped fabric, and the inner layer is formed from a foam material. The foam is compressed to form large central depressions which provide additional clearance between the eye covering and the infant's eyes. The mask is held in place by a headgear using a stretch gauze, or knit material. Yet, this mask has a number of drawbacks. For instance, this mask is still prone to misalignment. The large one-piece eye covering formed with outer layers made from a soft, napped fabric allows the eye covering to slide around. The eye covering also has a planar geometry which exacerbates this problem. Another drawback inherent in this design is that the planar geometry of this mask does a poor job of distributing forces about the infant's face which can potentially result in discomfort. Yet another drawback to this mask is that it does not conform to the complex geometry of the infant's face well. Leaving gaps between the infant's face and mask results in the potential for light to leak in under the mask.

Another mask, which further advanced the art, is described in U.S. Pat. No. 6,571,799. The mask described in this patent includes a two-part eye covering comprising an outer planar sheath having a pair of oval segments, or annular rings, connected to the rear surface of the planar sheath. The oval segments define cavities to provide clearance between the infant's eyes and the mask. The eye covering is held in place by a headgear, or bonnet, formed from a foam-type material. Unfortunately, this mask also has many of the same drawbacks noted above with respect to the '502 patent. This eye covering is once again formed having outer layers made from fabric. The resulting low coefficient of friction between the infant's face and mask allows the eye covering to slide around. Another drawback inherent in this design is that the geometry of this mask does a poor job of distributing forces about the infant's face which can potentially result in discomfort. Yet another drawback to this mask is that its geometry does not conform to the complex geometry of the infant's face well. Leaving gaps between the infant's face and mask results in the potential for light to leak in under the mask.

SUMMARY OF THE INVENTION

Accordingly, it is an object of the present invention to provide phototherapy goggles that overcome one or more of the shortcomings of conventional phototherapy goggles. This object is achieved according to one embodiment of the present invention by providing an assembly that may be used to cover the eyes of an infant undergoing phototherapy. The goggles may include an eye covering to cover the infant's eyes and headgear to secure the eye covering in place and thus prevent misalignment.

The eye covering may have an outer surface and an inner surface. The inner surface is contoured to correspond with the anatomical features of the infant's face to better distribute the strapping force exerted by the headgear about the infant's face. Since the contours correspond with the anatomical features of the infant's face, the eye covering also isolates the infant's eyes and minimizes the potential for light to leak in under the eye covering. In addition, by conforming to the contours of the infant's face, the eye covering is held in place better than goggles which do not conform to the complex shape of the infant's face.

The phototherapy goggles of the present invention may include a headgear assembly having an inner surface and an outer surface. The inner surface of the headgear assembly is configured to grip the infant's head. This feature of the invention further minimizes the potential for the eye covering to become misaligned. The headgear may be engaged with the eye covering to keep the eye covering properly aligned.

In another aspect, the present invention may be an eye covering for use in phototherapy goggles. The eye covering may be a pair of regions which are joined together by a bridge portion. The eye covering may be defined as an outer surface and an inner surface wherein the inner surface is anatomically contoured.

In yet another aspect, the present invention may be a headgear assembly. The headgear assembly may be a central portion and a pair of arms extending from the central portion. The central portion may be a fabric layer and an elastomeric layer. Hook tabs are attached to the arms. The fabric layer provides a surface which may be engaged by the hook tabs to hold the goggles in place. The elastomeric layer grips the infant's head to further minimize the potential of the headgear to become misaligned.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 7 is a rear elevational view of the headgear of the phototherapy goggles;

FIG. 8 is a front elevational view of an alternative embodiment of the headgear;

FIG. 9 is a partial cross-sectional view of the headgear along line 9-9 of FIG. 7;

FIG. 10 is a partial cross-sectional view of the headgear along line 10-10 of FIG. 8;

DETAILED DESCRIPTION OF THE EXEMPLARY EMBODIMENTS

Figure 1:
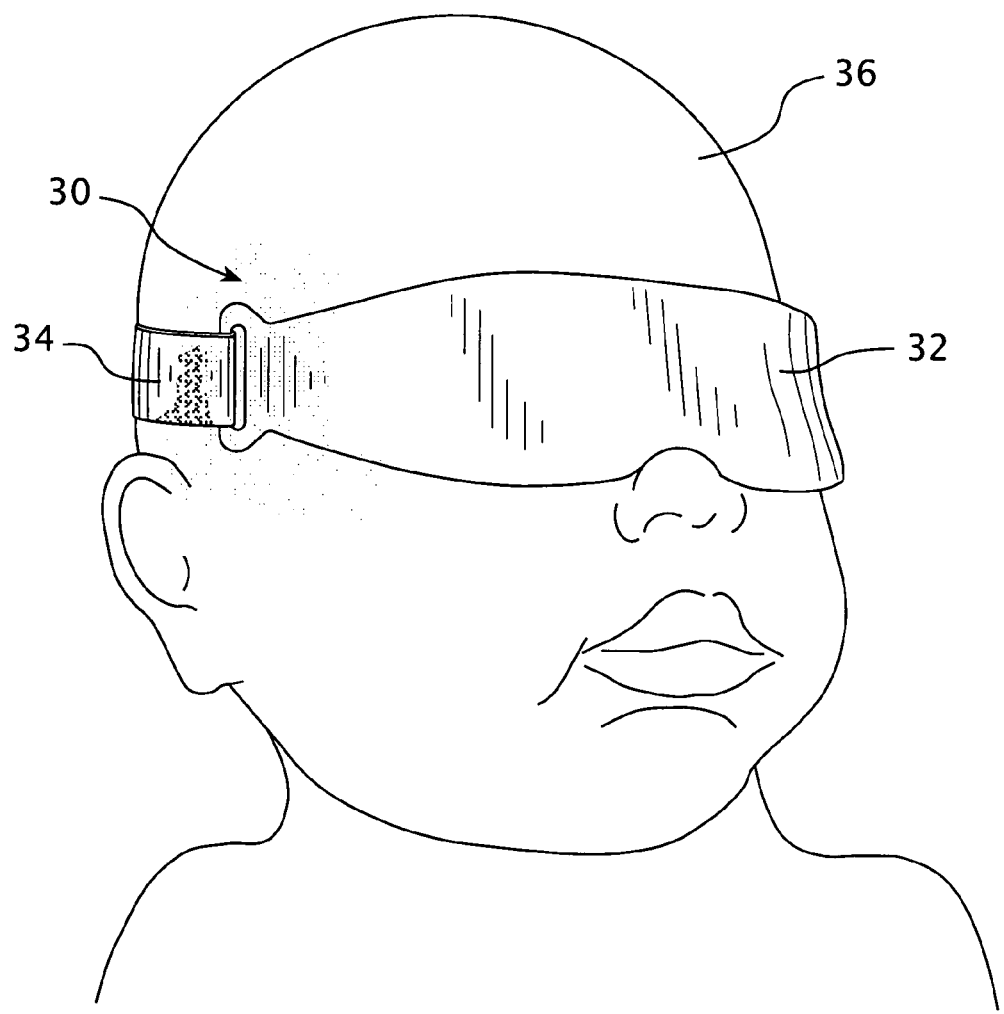
FIG. 1 is a front perspective view of phototherapy goggles located on an infant.
Figure 2:
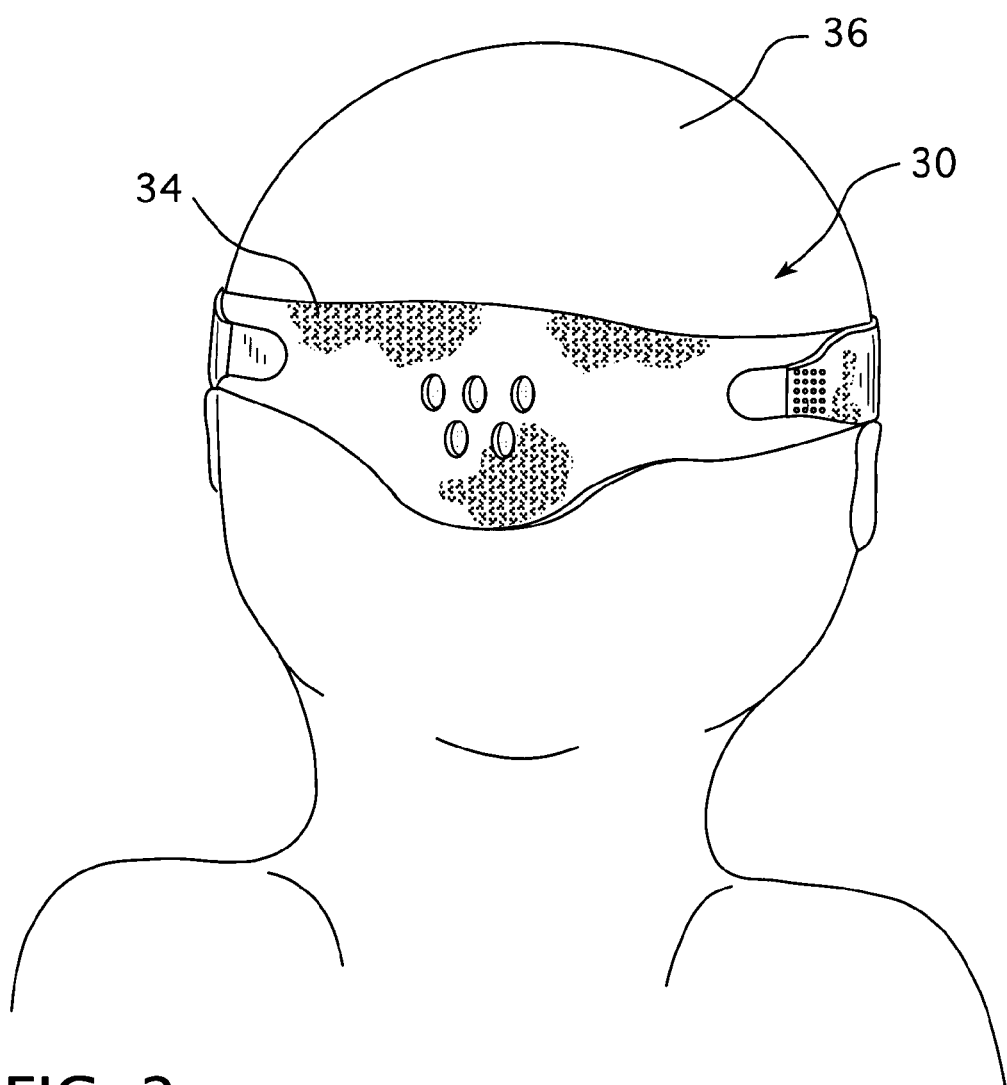
FIG. 2 is a rear perspective view of the phototherapy goggles located on an infant.

FIG. 1 schematically illustrates an exemplary embodiment of phototherapy goggles 30 according to the principles of the present invention. The phototherapy goggles include an eye covering 32 attached to a headgear 34 for use on an infant 36. The eye covering is configured to shield an infant's eyes while the headgear is configured to secure the eye covering 32 in place. While this invention has been described for use with infants, the inventors recognize that the unique aspects of the present invention could also be employed with individuals of any age. As seen in FIG. 2, the headgear is wrapped around the infant's head and secured to hold the eye covering in place.

Figure 3:
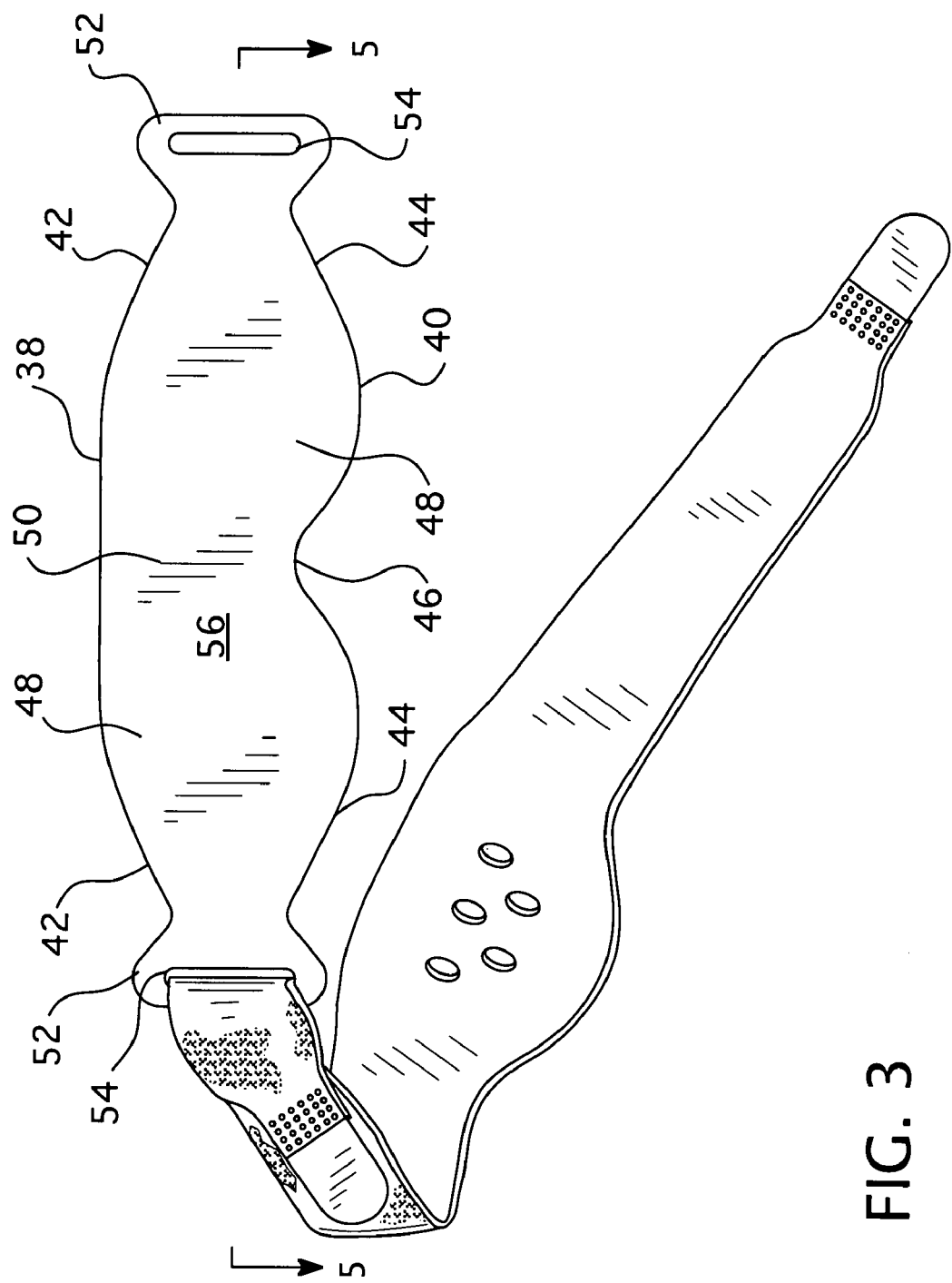
FIG. 3 is a front perspective view of the phototherapy goggles.
Figure 4:
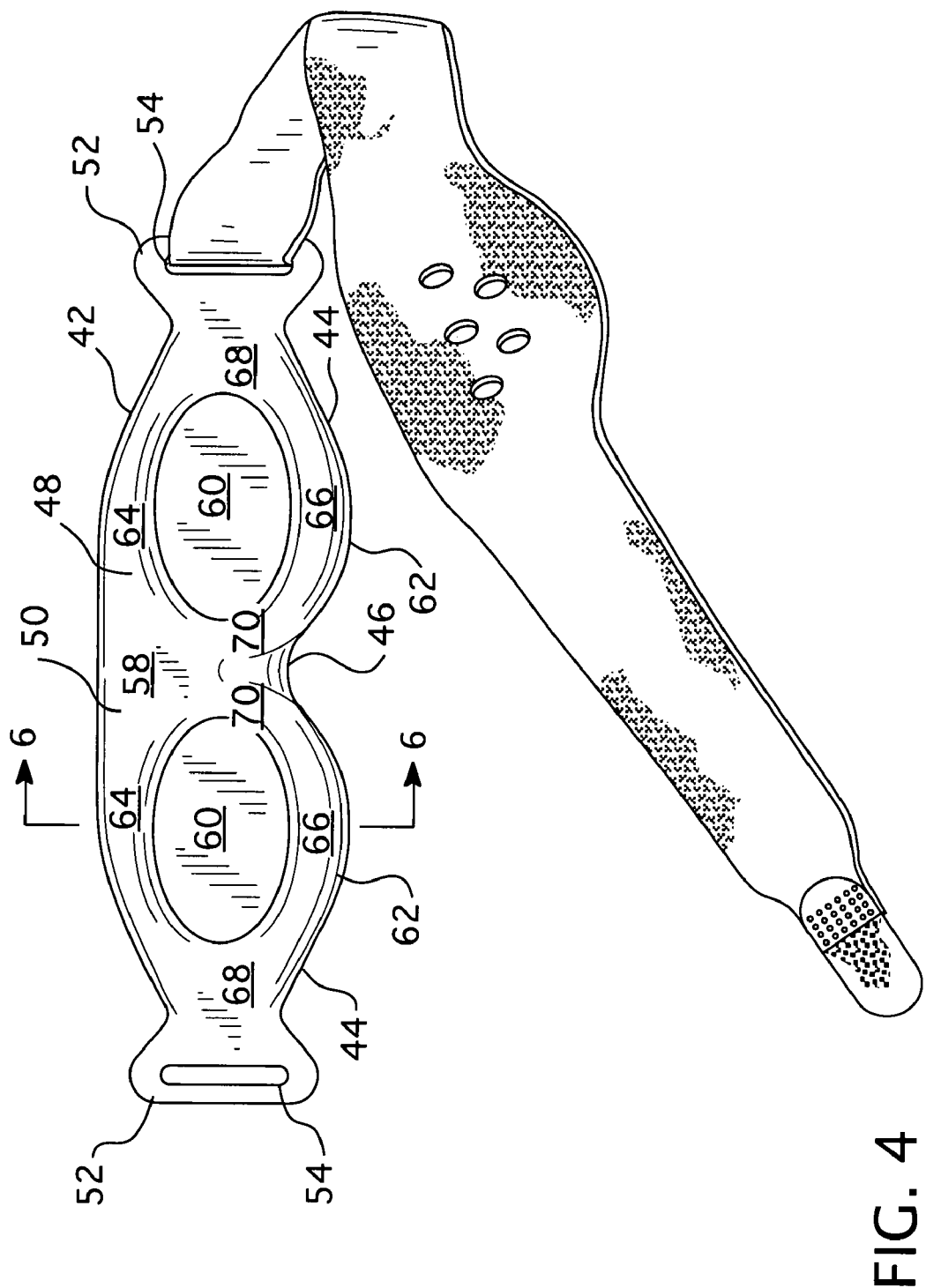
FIG. 4 is a rear perspective view of the phototherapy goggles.

With reference to FIGS. 3 and 4, the eye covering 32 has a superior border 38 and an inferior border 40. The superior border 38 includes a pair of tapered portions 42 while the inferior border 40 includes a pair of corresponding tapered portions 44 and a nasal groove 46 to provide clearance for the infant's nose. Without the nasal groove, the eye covering would cover the infant's nose and potentially result in discomfort to the infant. Additionally, the nasal groove provides lateral alignment of the eye covering. If a force is exerted on the eye covering in a lateral direction, the eye covering is held in place by the infant's nose. In addition, the nasal groove permits the mask to fit closer to the infant's face and thus minimize the potential for light to leak in under the eye covering. Together, tapered portions 42, tapered portions 44, and nasal groove 46 define two regions 48 joined together by a bridge portion 50. Regions 48 are shaped to roughly correspond with the orbital sockets of the infant. The eye covering also includes ears 52 adjacent regions 48. In one embodiment, the ears include slots 54 for receipt of the headgear.

The eye covering further includes an outer surface 56 and an inner surface 58. The outer surface is substantially planar while the inner surface is substantially contoured. The contours of the inner surface may be best appreciated with particular reference to FIGS. 4-6. Generally, the inner surface 58 is contoured to correspond to the anatomical features of the infant. Specifically, each region 48 of the inner surface includes a depression 60 surrounded by a raised portion 62. The depression provides clearance for the infant's eyes while the raised portion conforms to the anatomical features of the infant's face. The raised portions are defined by a supraorbital portion 64 located in the region above the infant's eyes, a infraorbital portion 66 located in the region below the infant's eyes, a zygomatic portion 68 located in the region adjacent the infant's zygomatic bone, and a nasal portion 70 located in the region adjacent the infant's nasal bone.

Figure 5:
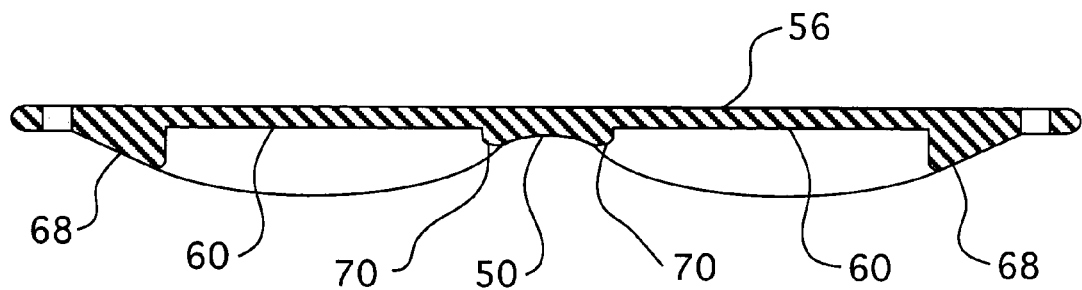
FIG. 5 is a cross-sectional view of the eye covering of the phototherapy goggles along line 5-5 of FIG. 3.
Figure 6:
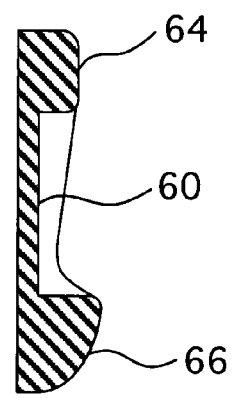
FIG. 6 is a cross-sectional view of the eye covering of the phototherapy goggles along line 6-6 of FIG. 4.

With reference to FIGS. 5 and 6, the relative size and shape of each portion of the eye covering are shown. The zygomatic portions extend a distance outward while the nasal portions extend a lesser distance outward. Similarly, the infraorbital portion extends a distance outward while the supraorbital portion extends a lesser distance outward. Of course, each portion is not discrete. Instead, each portion smoothly transitions into the adjacent portions.

Turning now to FIGS. 7-10, the headgear of the phototherapy goggles includes a central portion 72 and arms 74. The arms extend outwardly and are angled downwardly. Extending from the arms are hook tabs attached via welds 77. The inventors contemplate that the welds may be any vibrational weld such as RF welds, ultrasonic welds, and the like. The headgear has an upper edge 78 and a lower edge 80. The lower edge bulges outwardly to form a projecting region 82 in the central portion. In addition, the central portion has holes 84 to provide additional flexibility in this region. In use, the central portion may deform to accommodate the unique shape of the infant's head and thus minimize the potential of the headgear to slide around on the infant's head. The headgear has an outer surface 86 and an inner surface 88. To further facilitate the flexibility of the headgear, the headgear is formed from a flexible material such as fabric with a loop pile on the outer surface. The headgear may be secured in place by threading arms 74 through slots 54. The arms are then pulled taut. Once the headgear is taut, hook tabs 76 may be pressed into the loop pile of the outer surface 86 to hold the headgear in place. Alternatively, the eye covering could be held in place by an adhesive applied between the eye covering and the infant. One common adhesive used in the art is a hydrogel adhesive. However, the inventors contemplate that a variety of other adhesives could be used.

The headgear may be formed from a material which minimizes the potential for the headgear to slide around. As best appreciated with reference to FIG. 9, the headgear may be formed from a material having multiple layers such as a fabric layer 90, and an elastomeric layer 92. The fabric layer may be engaged by the hook tabs. The elastomeric layer may be formed from a foam material such as the Fabrifoam® composite material sold by Applied Technology International, Ltd. such that the elastomeric layer 92 has a sufficient coefficient of friction which grips the infant's head while the fabric layer 90 provides a loop pile for the hook portion 76. In addition, the foamed material may result in a headgear which is lighter and more comfortable for the infant.

In an alternative embodiment, as best appreciated with reference to FIGS. 8 and 10, the headgear can be formed using more than one material. For instance, the headgear may be formed with the central portion 72 from one material and the arms 74 from another material. As seen in FIG. 10, the central portion may once again have a fabric layer 90 and an elastomeric layer 92. However, arms 74 may be formed from a second fabric layer 94 without a corresponding elastomeric layer. This provides many of the same benefits of the previous design while utilizing a lighter and less costly material for the arms. In this embodiment, the arms are joined to the central portion via welds 96.

Figure 11:
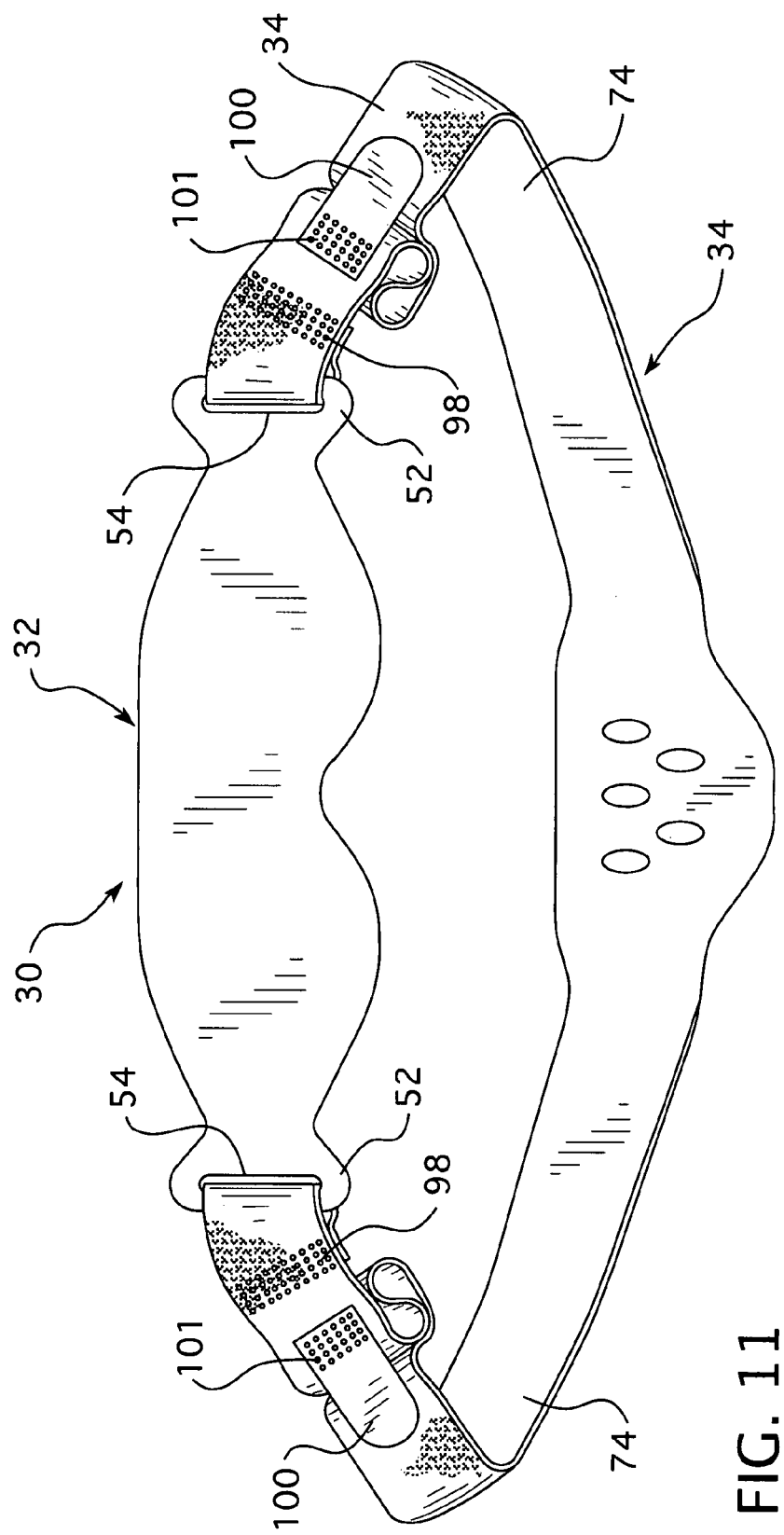
FIG. 11 is a front perspective view of an alternative embodiment of the phototherapy goggles.

Another alternative embodiment is shown in FIG. 11. In this embodiment, the headgear is attached to the eye covering and held in place via welds 98. The arms also include hook tabs 100 which face inwardly. Welds 101 are used to attach hook tabs 100 to arms 74. In order to adjust the size of the headgear the arms are bunched-up, or pleated, to shorten the length of the arms. Once the appropriate length is obtained, each hook tab is engaged with the corresponding arm. One unique aspect of an embodiment of the present invention is that it may simplify the process of donning the phototherapy goggles. The caregiver simply slides the infant's head between the eye cover and the headgear. To hold the goggles in place, the hook tabs are engaged at the appropriate location along the headgear. This configuration allows the caregiver to put the goggles on the infant without having to thread the arms of the headgear through slots or be forced to handle separate pieces.

Figure 12:
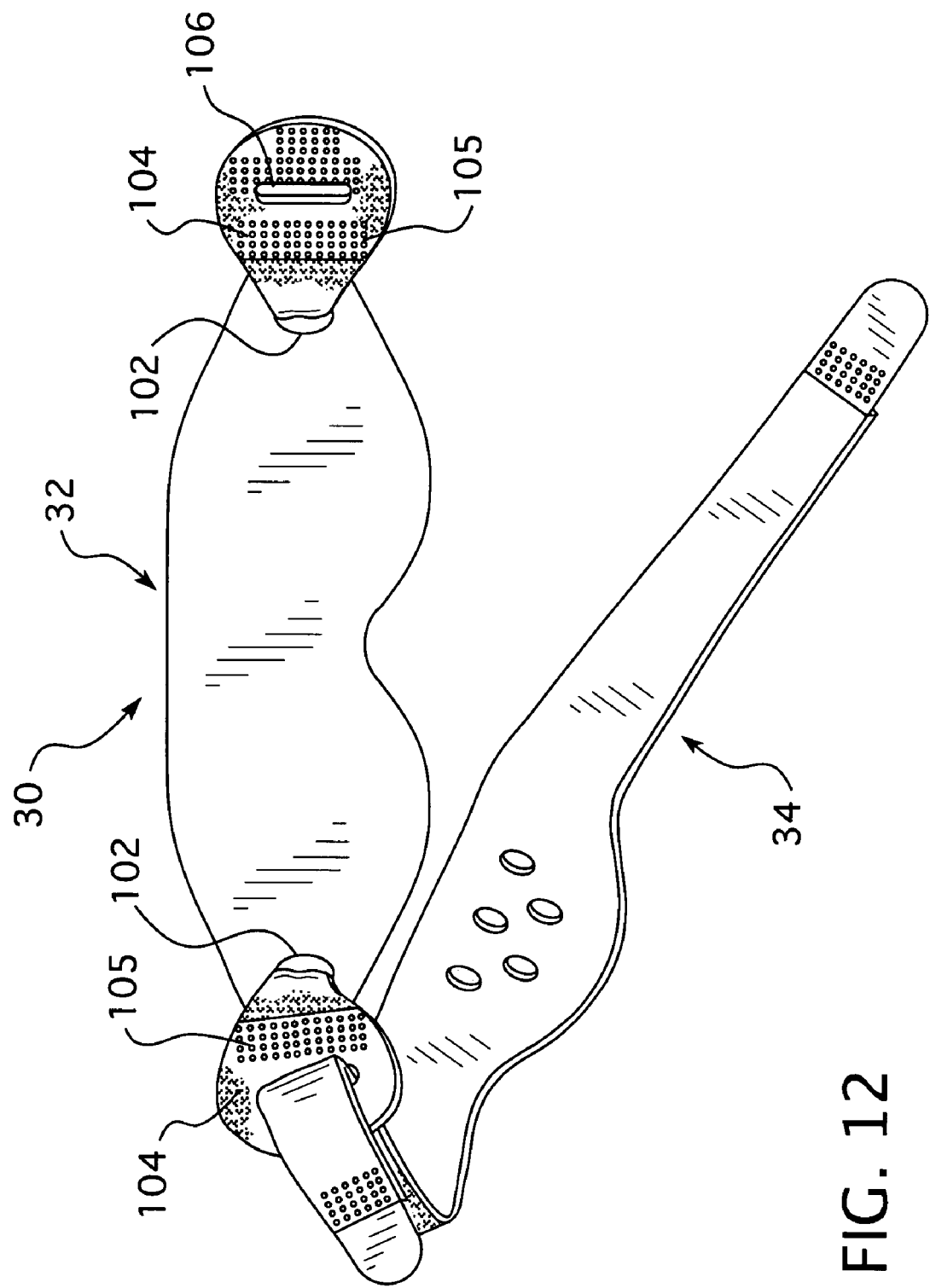
FIG. 12 is a front perspective view of an alternative embodiment of the phototherapy goggles.
Figure 13:
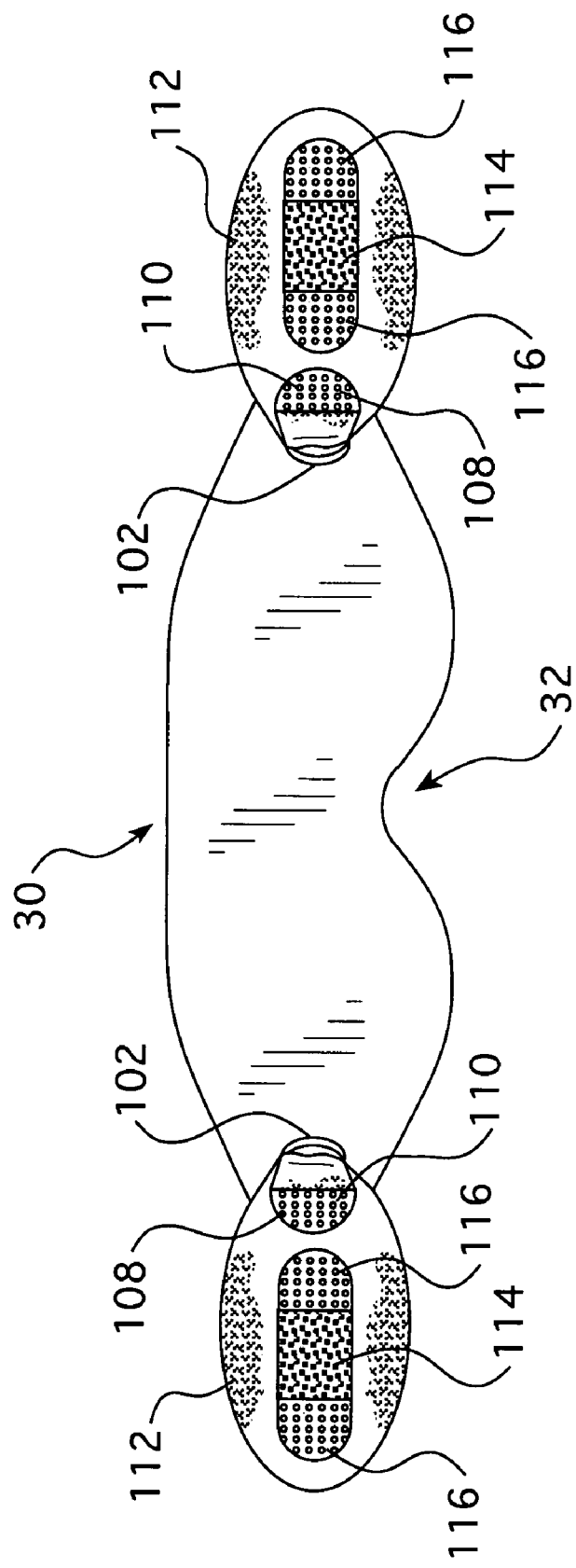
FIG. 13 is a front elevational view of an alternative embodiment of the phototherapy goggles.

Another alternative embodiment is shown in FIG. 12. In this embodiment, the eye covering 32 has openings 102. Fitted through openings 102 are flaps 104. Each flap is constructed from a piece of sheet material which is passed through the opening and folded back upon itself and attached together via welds 105. These flaps include a slot 106 through which the arms of the headgear may be threaded. Another alternative embodiment is shown in FIG. 13. In this embodiment, the eye covering 32 once again has openings 102. This design differs from the previous design in that it includes flaps 108 attached via welds 110 to pads 112. The pads include hook tabs 114 affixed to the pads by welds 116. The pads operate to at least partially cover the hook tabs to minimize the potential for the hooks to contact the infant's skin.

While the phototherapy goggles of the present invention have been described as using vibrational welds, one of ordinary skill in the art can best appreciate that a variety of other joining methods may be utilized without departing from the teachings of the present invention. For instance, the present invention contemplates that the various welds could be replaced by an adhesive, or even sewing the various parts together.

In one aspect, in order to manufacture the above described invention, the eye covering is die cut along superior border, inferior border, and about the ears from planar material. The die-cutting step may include either simultaneously, or subsequently, die-cutting the slots. Next, the contours are molded into the foam by compressing the foam in a heated mold (commonly known as felting). Once the part is cooled, the eye covering will retain a molded shape. As an alternative to forming the eye covering by felting, the eye covering could be formed by injecting expandable foam into a mold or even by some type of laminate construction built from layers of material. The material used for the eye covering may be selected from a variety of materials such as polyurethane, polyester, thermoplastic elastomers, or even viscoelastic foam. Of course a variety of other materials may be utilized such as fabric and the like. The inventors contemplate that any material which can be felted or expansion molded to create the desired contours may be utilized without departing from the scope of the present invention.

The headgear may also be formed by die-cutting the headgear from sheet material. In the embodiment shown in FIG. 7, the headgear is die-cut from a single sheet of material. Thus, the arms 74 are formed integrally with the central portion 72. This die-cutting step may include simultaneously, or sequentially, die cutting the holes. As for the embodiment shown in FIG. 8, the central portion may be cut from one material and the arms may be cut from another material. Next the arms are then attached to the central portion by welding the central portion to the arms. The next step includes attaching the hook tabs to the arms. However, as noted above, the inventors contemplate that the various steps of joining parts together may be achieved by adhering, sewing, or any other similar attachment method. The material used for the central portion of the headgear may have an elastomeric layer selected from a variety of materials such as polyurethane, silicon, thermoplastic elastomers. Of course a variety of other materials may be utilized. The inventors contemplate that any material which provides a sufficient coefficient of friction may be used without departing from the scope of the present invention. The material for the fabric layer may be any fabric compatible for use with infants. In the event that the arms are formed from a dual layer material, the same materials utilized to form the fabric layer and the elastomeric layer may be used. Alternatively, as noted above, the arms may be constructed having a second fabric layer 94. This fabric layer may be constructed from any fabric that is compatible for use with infants. Preferably, the fabric has at least one surface that has a loop pile.

As best appreciated by one of ordinary skill in the art, this configuration provides several advantages over the prior art. Due to the anatomical shape of the eye covering, the eye covering of the present invention is able to distribute the forces exerted on the eye covering, able to block light, and seats better on the face of the user to prevent misalignment.

The headgear of the present invention also has a number of advantages. For instance, use of an elastomeric with a high coefficient of friction results in phototherapy goggles that are less prone to misalignment if the infant chooses to move around. Phototherapy goggles having an elastomeric layer with a higher coefficient of friction adjacent the infant's head minimizes the potential of the goggles to become misaligned.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An assembly for fitting on a user's head for precluding exposure of a user's eyes to light, wherein the assembly comprises:
    a unitary eye covering formed from a single piece of material, the eye covering having an outer surface and an inner surface, the eye covering precluding light from passing therethrough to the eyes of a user when worn by a user, wherein the inner surface is anatomically contoured; and
    headgear having an inner surface and an outer surface, the headgear being engaged with the eye covering to keep the eye covering properly aligned,
    wherein the eye covering has a two regions, each region having a depression surrounded by a raised portion, and wherein the depression and raised portion are integrally formed in the eye covering.

2. The assembly as recited in claim 1, wherein the raised portion is defined by a supraorbital portion, an infraorbital portion, a zygomatic portion, and a nasal portion.

3. The assembly as recited in claim 2, wherein the raised portions of each region are sized and shaped to conform to the corresponding shape of the user's head.

4. The assembly as recited in claim 1, wherein the eye covering further comprises ears having openings.

5. The assembly as recited in claim 4, wherein the openings are elongated slots.

6. The assembly as recited in claim 5, wherein the headgear comprises:
    a central portion; and
    a pair of arms extending from the central portion.

7. The assembly as recited in claim 6, wherein the central portion comprises a fabric layer and an elastomeric layer.

8. The assembly of claim 1, wherein the eye covering, including the inner and outer surfaces, are integrally molded with each other.

9. The assembly of claim 1, wherein a thickness of the eye covering varies such that the eye covering is constructed and arranged to cause the inner surface of the eye covering to conform to a user's anatomical facial features when worn by a user and thereby reduce an amount of light reaching a user's eyes via light leakage between the eye covering and a user's face.

10. An eye covering for phototherapy goggles, the eye covering comprising:
    a pair of regions; and
    a bridge region joining the pair of regions together, wherein the eye covering has an outer surface and an inner surface, and wherein the inner surface is anatomically contoured, wherein the eye covering is formed from a single piece of material, and wherein the eye covering precludes light from passing therethrough to the eyes of a user when worn by a user,
    wherein each of the pair of regions comprises a depression surrounded by a raised portion formed integrally in the eye covering, wherein each raised portion has a supraorbital portion, an infraorbital portion, a zygomatic portion, and a nasal portion.

11. An eye covering as recited in claim 10, wherein the eye covering is formed from a foam material.

12. An eye covering as recited in claim 10, wherein the depression and the raised portion are formed by felting the foam material.

13. An eye covering as recited in claim 10, in combination with:
    a headgear assembly comprising:
        a central portion, the central portion having a fabric layer and an elastomeric layer;
        a pair of arms extending from the central portion; and
        hook tabs attached to the arms.

14. The combination recited in claim 13, wherein the arms are formed integrally with the central portion from a single piece of material.

15. The combination recited in claim 13, wherein the arms are attached to the central portion.

16. The combination recited in claim 15, wherein the tabs are attached to the arms and the arms are attached to the central portion by vibrational welding.

17. The combination recited in claim 13, wherein the tabs are attached to the arms and the arms are attached to the central portion by ultrasonic welding.

18. The eye covering of claim 10, wherein the pair of regions and bridge region are integrally molded with each other.

19. The eye covering of claim 10, wherein the supraorbital portion of each of the pair of regions extends outwardly less than the infraorbital portion of the respective region.

20. An eye covering for phototherapy goggles, the eye covering comprising:
    a pair of regions; and
    a bridge region joining the pair of regions together, wherein the eye covering has an outer surface and an inner surface, and wherein the inner surface is anatomically contoured, wherein the eye covering is formed from a single piece of material, and wherein the eye covering precludes light from passing therethrough to the eyes of a user when worn by a user,
    wherein each of the pair of regions comprises a depression surrounded by a raised portion formed integrally in the eye covering, and wherein the depression and raised portion are integrally formed in the eye covering.

* * * * *